(12) United States Patent
Sano et al.

(10) Patent No.: US 9,782,127 B2
(45) Date of Patent: Oct. 10, 2017

(54) PHOTOELECTRIC SPHYGMOGRAPH MEASUREMENT DEVICE

(75) Inventors: Satoshi Sano, Kawasaki (JP); Takayuki Yamaji, Kawasaki (JP); Yasuhiko Nakano, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 991 days.

(21) Appl. No.: 13/169,480

(22) Filed: Jun. 27, 2011

(65) Prior Publication Data

US 2011/0257534 A1 Oct. 20, 2011

Related U.S. Application Data

(63) Continuation of application No. PCT/JP2009/051438, filed on Jan. 29, 2009.

(51) Int. Cl.
*A61B 5/02* (2006.01)
*A61B 5/00* (2006.01)
*A61B 5/024* (2006.01)

(52) U.S. Cl.
CPC ........ *A61B 5/6816* (2013.01); *A61B 5/02427* (2013.01); *A61B 2560/0209* (2013.01)

(58) Field of Classification Search
CPC .............. A61B 5/6816; A61B 5/14551; A61B 5/02416; A61B 5/1455; A61B 5/6826;
(Continued)

(56) References Cited

U.S. PATENT DOCUMENTS

| | | | | |
|---|---|---|---|---|
| 4,063,551 A | * | 12/1977 | Sweeney | ............ A61B 5/02416 600/479 |
| 6,608,562 B1 | * | 8/2003 | Kimura | .............. A61B 5/02427 128/903 |

(Continued)

FOREIGN PATENT DOCUMENTS

| | | |
|---|---|---|
| EP | 0198573 | 10/1986 |
| JP | 61-187836 | 8/1986 |

(Continued)

OTHER PUBLICATIONS

International Search Report mailed Feb. 24, 2009, for International Application No. PCT/JP2009/051438.

*Primary Examiner* — Navin Natnithithadha
*Assistant Examiner* — Eric Messersmith
(74) *Attorney, Agent, or Firm* — Staas & Halsey LLP

(57) ABSTRACT

A photoelectric sphygmograph measurement device includes a light emitting part emitting light pulses, a light receiving part having a light receiving element that receives the light pulses and producing a corresponding output signal, and a control part driving the light emitting part to emit the light pulses and performing a pulse wave measurement by using the output signal. The control part drives the light emitting part so that a charge accumulated in the light emitting element converges on a predetermined amount in a case where the charge accumulated in the light receiving element decreases to the predetermined amount or less during a time when driving of the light emitting part is stopped and/or in a case where the light receiving element changes to a first state in which the light receiving element is capable of receiving the light pulses from a second state in which the light receiving element is not capable of receiving the light pulses.

4 Claims, 9 Drawing Sheets

(58) Field of Classification Search
CPC ..... A61B 5/7282; A61B 5/024; A61B 5/0295; A61B 5/7203; A61B 5/02438; A61B 5/026; A61B 5/1495
USPC .................................................. 600/500–509
See application file for complete search history.

(56) References Cited

U.S. PATENT DOCUMENTS

| | | | | |
|---|---|---|---|---|
| 2004/0054269 | A1* | 3/2004 | Rantala | A61B 5/14551 600/322 |
| 2005/0187446 | A1* | 8/2005 | Nordstrom | A61B 5/14551 600/323 |
| 2009/0259116 | A1* | 10/2009 | Wasserman | A61B 5/14551 600/323 |

FOREIGN PATENT DOCUMENTS

| | | |
|---|---|---|
| JP | 64-27532 | 1/1989 |
| JP | 2001-70266 | 3/2001 |

\* cited by examiner

PHOTOELECTRIC SPHYGMOGRAPH MEASUREMENT DEVICE

CROSS-REFERENCE TO RELATED APPLICATION

This application is a continuation application of PCT/JP2009/051438 filed Jan. 29, 2009, the contents of which are herein wholly incorporated by reference.

FIELD

A certain aspect of the embodiments disclosed herein is related to a photoelectric sphygmograph measurement device.

BACKGROUND

Conventionally, as a method for measuring the pulse rate, there is known a method that detects an electrocardiographic signal that produces a heartbeat. Recently, there has been used a method for measuring the pulse rate (photoelectric sphygmograph measurement device), which method detects the amount of light absorption that varies in accordance with a change in the volume of an artery caused by a heartbeat (pulse wave).

The photoelectric sphygmograph measurement device projects a fixed amount of light onto a human body, detects remaining light other than the light absorbed by blood, and measures a variation in the remaining light.

As to the photoelectric sphygmograph measurement device, there is a proposal directed to reduction in power consumption and configured to determine whether the measurement of pulse wave is in progress by using the incident level of the light detected and to stop projecting light or decrease the amount of emission of light when the measurement is not in progress (see Japanese Laid-Open Patent Publication No. 1-27532).

However, the proposal have the following issues. The complete stop of the light projection during the time when the measurement of pulse wave is not in progress may consume a long time until it becomes ready for detecting light by the photoelectric element after the measurement of pulse wave is restarted. In the photoelectric element, it may take a long time to accumulate a certain amount of charge.

A similar problem may occur in a case where the measurement of pulse wave becomes possible after a situation in which the photoelectric element is not capable of receiving light continues for a long time.

SUMMARY

According to an aspect of the present invention, there is provided a photoelectric sphygmograph measurement device including: a light emitting part configured to emit light pulses; a light receiving part configured to have a light receiving element that receives the light pulses emitted by the light emitting part and to produce an output signal corresponding to the light pulses received by the light receiving element; and a control part configured to drive the light emitting part to emit the light pulses and perform a pulse wave measurement on the basis of the output signal of the light receiving part, the control part driving the light emitting part so that a charge accumulated in the light emitting element converges on a predetermined amount in a case where the charge accumulated in the light receiving element decreases to the predetermined amount or less during a time when driving of the light emitting part is stopped and/or in a case where the light receiving element changes to a first state in which the light receiving element is capable of receiving the light pulses from a second state in which the light receiving element is not capable of receiving the light pulses.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

A description is now given of an embodiment of the present invention with reference to FIGS. 1 through 7.

Figure 1:
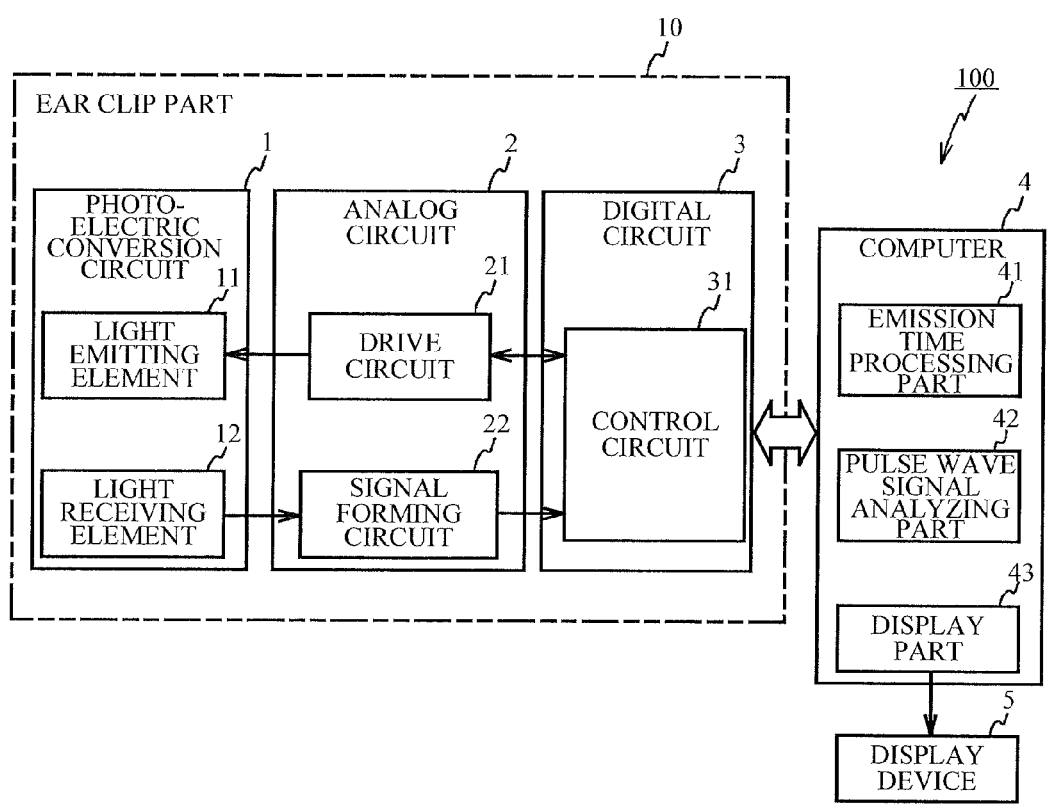
FIG. 1 is a block diagram of a photoelectric sphygmograph measurement device in accordance with an embodiment.

FIG. 1 is a block diagram of a photoelectric sphygmograph measurement device 100 in accordance with an embodiment. The photoelectric sphygmograph measurement device 100 is of ear clip type, and includes a clip type sensor (ear clip part) wearable on an ear of human being (testee). The device 100 detects the pulse wave of the testee with the ear clip part 10 that is worn on the ear of the testee who may be taking exercise such as running, and obtains biological information produced by a blood pressure change by a heartbeat or an increase or decrease in the blood flow.

As illustrated in FIG. 1, the photoelectric sphygmograph measurement device 100 includes a photoelectric conversion circuit 1, an analog circuit 2, a digital circuit 3, a computer 4 and a display device 5. The above parts except the computer 4 and the display device 5 are installed in the ear clip part 10, which is worn on the ear of the testee. The ear clip part 10 is connected to the computer via wires (interconnections). The computer 4 may be installed in the cellular phone or portable terminal equipment, and the display device 5 may be a display of the portable information terminal.

The photoelectric conversion circuit 1 includes a light emitting element 11, which may be an exemplary light emitting part, and a light receiving element 12, which may be an exemplary light receiving part. For example, the light emitting element 11 includes an LED (Light Emission Diode) and emits light having a predetermined wavelength. The light having the predetermined wavelength may be near infrared light, for example. Light emitted by the light emitting element 11 is projected onto an artery of the ear, and is absorbed in and reflected by the artery. The light emitting element 11 is controlled by a control circuit 31 through the drive circuit 21, which will be described later, and intermittently emits light at intervals that are changed by a pulse wave.

The light receiving element 12, which may include a photodiode, for example, receives transmitted light out of the light emitted by the light emitting element 11 and produces an output signal corresponding to the transmitted light. The above output signal of the light receiving element 12 is an analog electric signal, which is output in the form of current. Preferably, the photodiode has a high linearity to the light (near infrared light) emitted by the light emitting element 11 and has a characteristic such that the pulse is not greatly affected in a biased state. For example, the photodiode may have a good dark current characteristic, that is, a good internal bias characteristic by generated charges. The signal output by the light receiving element 12 may be as illustrated in part (a) of FIG. 3.

Figure 2:
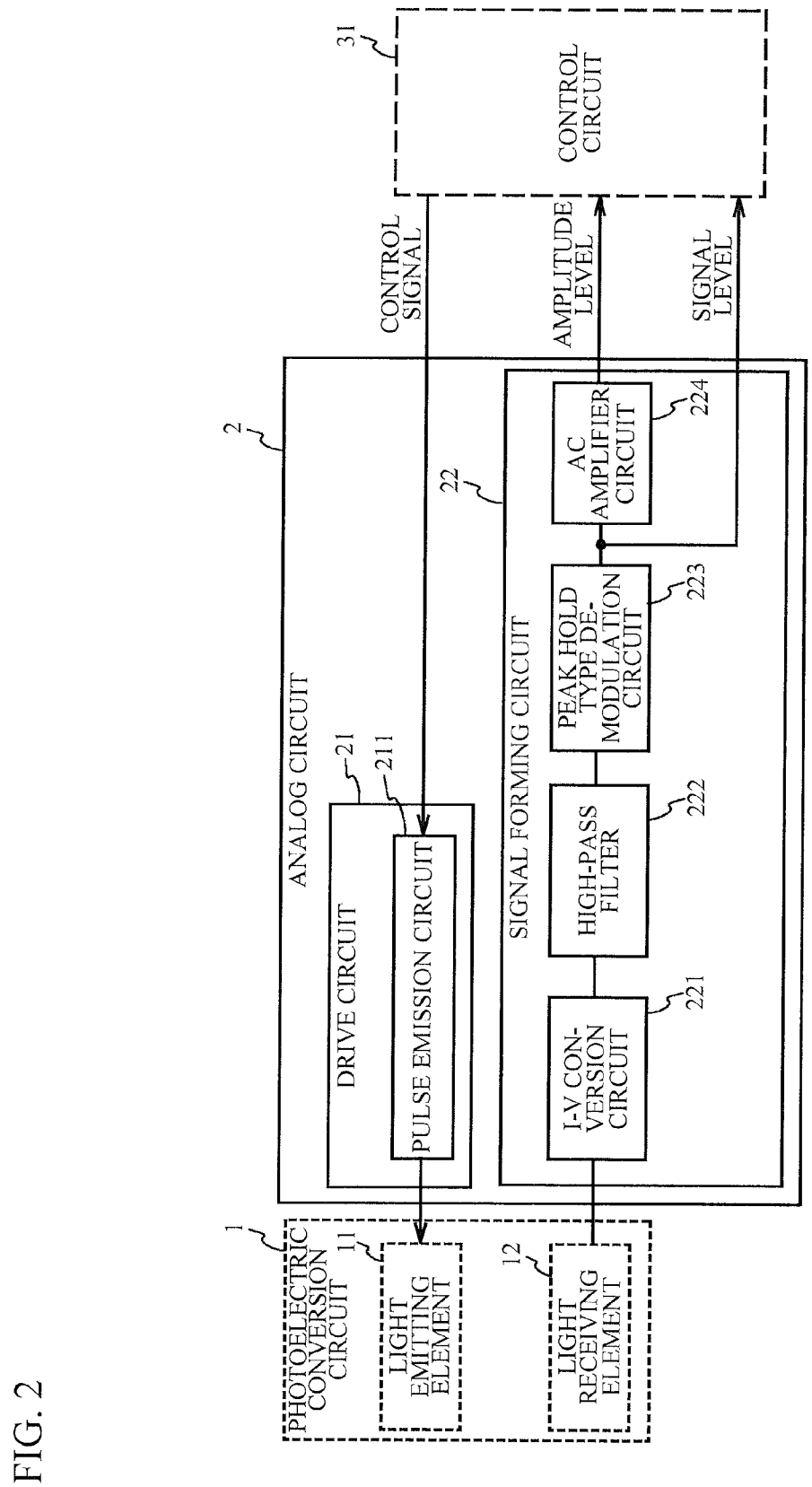
FIG. 2 is a block diagram of an analog circuit illustrated in FIG. 1.
Figure 3:
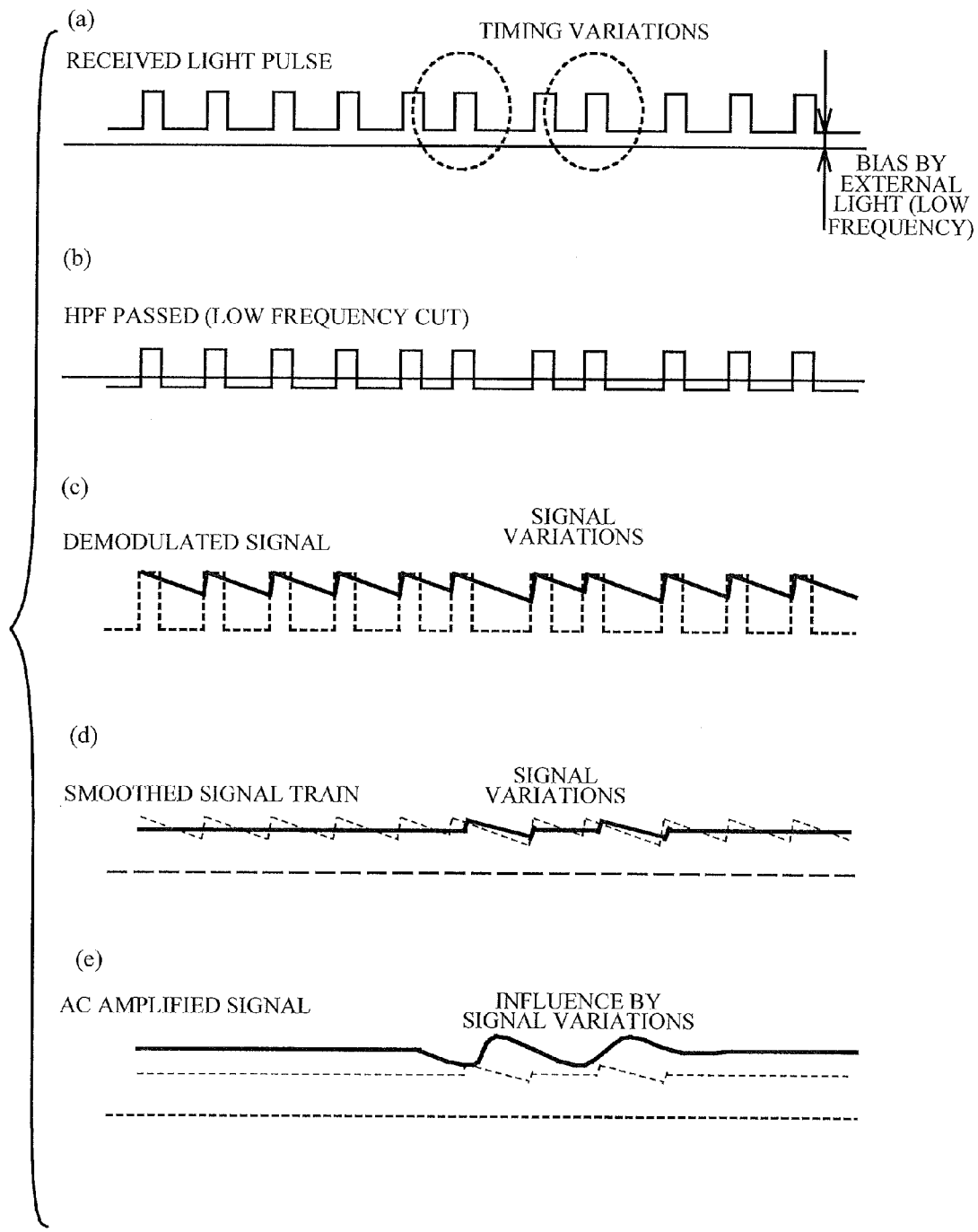
FIG. 3 is a waveform diagrams of signals observed in the block diagram of FIG. 1.

FIG. 2 is a block diagram of an exemplary structure of the analog circuit 2. As illustrated in FIG. 2, the analog circuit 2 includes a drive circuit 21 connected to the light emitting element 11, and a signal forming circuit 22 connected to the light receiving element 12.

The drive circuit 21 has a pulse emission circuit 211, which controls the emission of the light emitting element 11 in accordance with instructions from the control circuit 31.

The signal forming circuit 22 generates (forms) a continuous pulse wave signal based on the output signal of the light receiving element 12, and is composed of an I-V conversion circuit 221, a high-pass filter circuit 222, a peak hold type demodulation circuit 223 and an AC amplifier circuit 224, which may function as an extraction circuit.

The IV conversion circuit 221 converts the current from the light receiving element 12 into a corresponding voltage in analog form. The voltage is applied to the high-pass filter circuit 222, which effectively extracts only pulse components from the received pulse signal on which noise components biased by external light are superimposed. For example, the high-pass filter circuit 222 may have a 1000 MHz secondary cutoff for a pulse width of 20 μm in order to effectively remove variations by external light. The output signal from the high-pass filter circuit 222 may be as illustrated in part (b) of FIG. 3. The peak hold type demodulation circuit 223 uses a diode rectifying function to extract a voltage component of a peak signal output that passes through the high-pass filter circuit 222 having a predetermined level or higher. Then, the circuit 223 stores the above voltage component in a capacitor and holds the charge proportional to the peak signal. The output signal of the peak hold type demodulation circuit 223 depending on the charge accumulated in the capacitor may be as illustrated in part (c) of FIG. 3. When the peak becomes equal to or lower than the predetermined value, the capacitor may be discharged. The AC amplifier circuit 224 has a function of smoothing the output signal of the peak hold type demodulation circuit 223, as illustrated in part (d) of FIG. 3. The smoothed signal may have a predetermined frequency or lower (for example, 0.7 Hz~5 Hz). The AC amplifier circuit 224 amplifies the smoothed signal and outputs an AC amplified signal as illustrated in part (e) of FIG. 3.

The control circuit 31 of the digital circuit 3 receives, through A/D converts, the signal level of the demodulated signal from the peak hold type demodulation circuit 223 and the amplitude level of the output signal of the AC amplifier circuit 224, and carries out emission control by signal processing of the received signals.

Turning to FIG. 1 again, the computer 4 functionally has an emission time processing part 41, a pulse wave signal analyzing part 42, and a display part 43. The emission time processing part 41 determines a parameter involved in driving the photoelectric conversion circuit 1. The above parameter includes the emission time of the light emitting element 11. The pulse wave signal analyzing part 42 analyzes the pulse wave signal from the control circuit 31 to obtain information about heartbeat and another item, and outputs the information to the display part 43. The display part 43 is connected to the display device 5 and causes the information from the pulse wave signal analyzing part 42 to be displayed on the display device 5.

Figure 4:
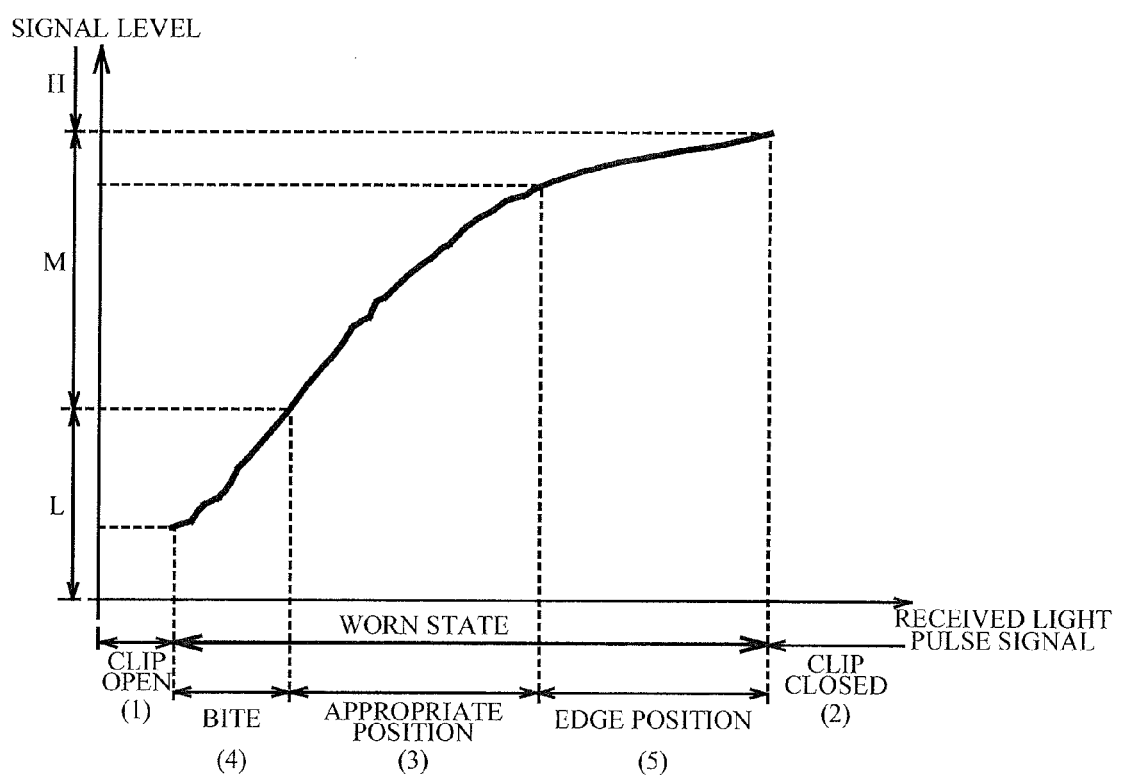
FIG. 4 is a graph that illustrates a relationship between a signal characteristic and a wearing state.

FIG. 4 illustrates a map that defines a relationship between the signal level of the demodulated signal from the peak hold type demodulation circuit 223 and the worn state of the ear clip part 10. By using the map as illustrated in FIG. 4, the control circuit 31 determines whether the ear clip part 10 is worn on an ear of the testee and determines how the ear clip part 10 is worn thereon on the basis of the level of the demodulated signal.

More particularly, the control circuit 31 may identify the following states in which the following reference numerals correspond to those in FIG. 4:

(1) a state in which the ear clip part 10 is not worn and is open (light from the light emitting element 11 is hardly incident to the light receiving element 12);

(2) a state in which the ear clip part 10 is not worn and is closed (almost all light from the light emitting element 11 is incident to the light receiving element 12);

(3) a state in which the ear clip part 10 is worn on an appropriate position (light from the light emitting element 11 is appropriately incident to the light receiving element 12);

(4) a state in which the ear clip part 10 is worn on an ear so as to bite a thick portion of the ear (a small mount of light out of the light from the light emitting element 11 is incident to the light receiving element 12); and (5) a state in which the ear clip part 10 is worn on an edge position of an ear (a large amount of light from the light emitting element 11 is incident to the light receiving element 12).

Figure 5A:
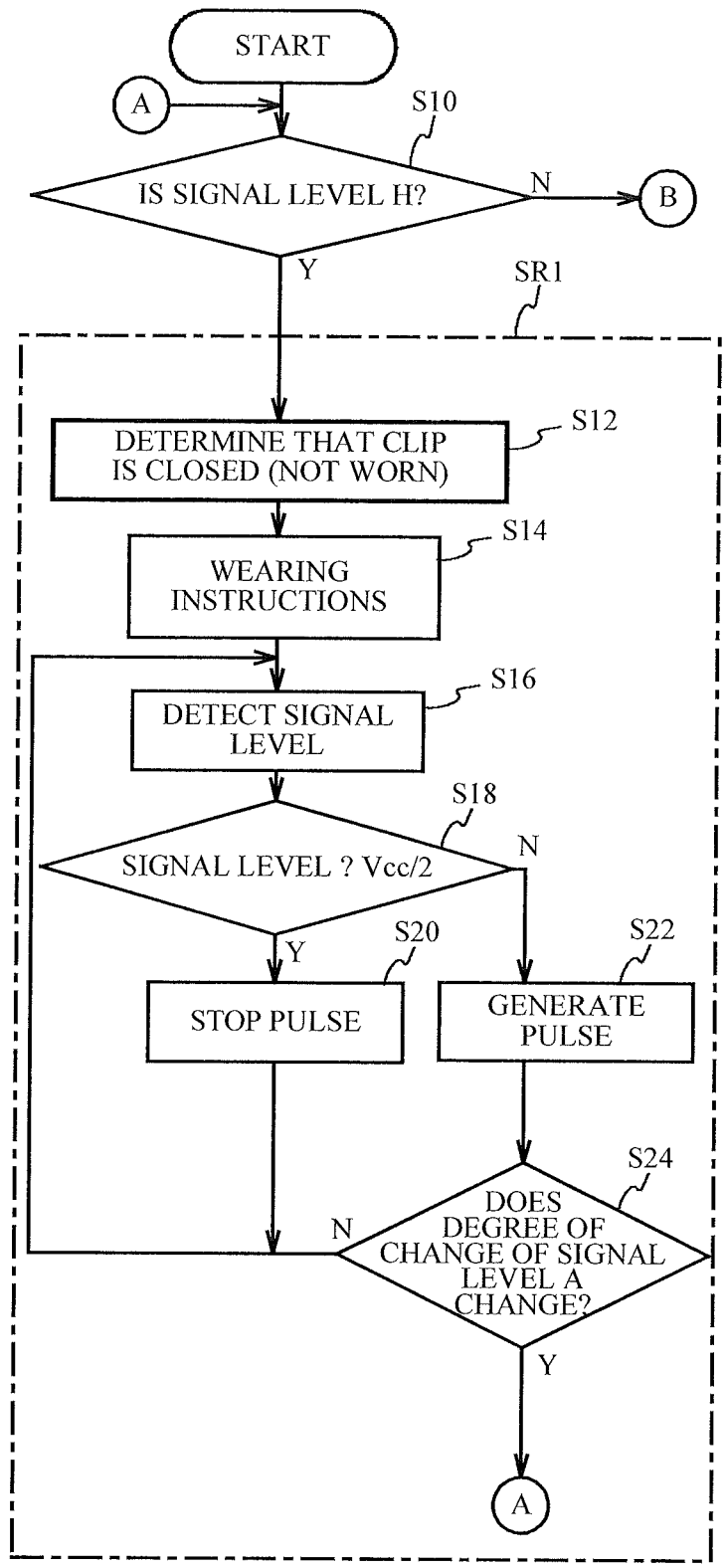
FIGS. 5A through 5C are flowcharts of a process before a pulse wave measurement is initiated (restarted)
Figure 5B:
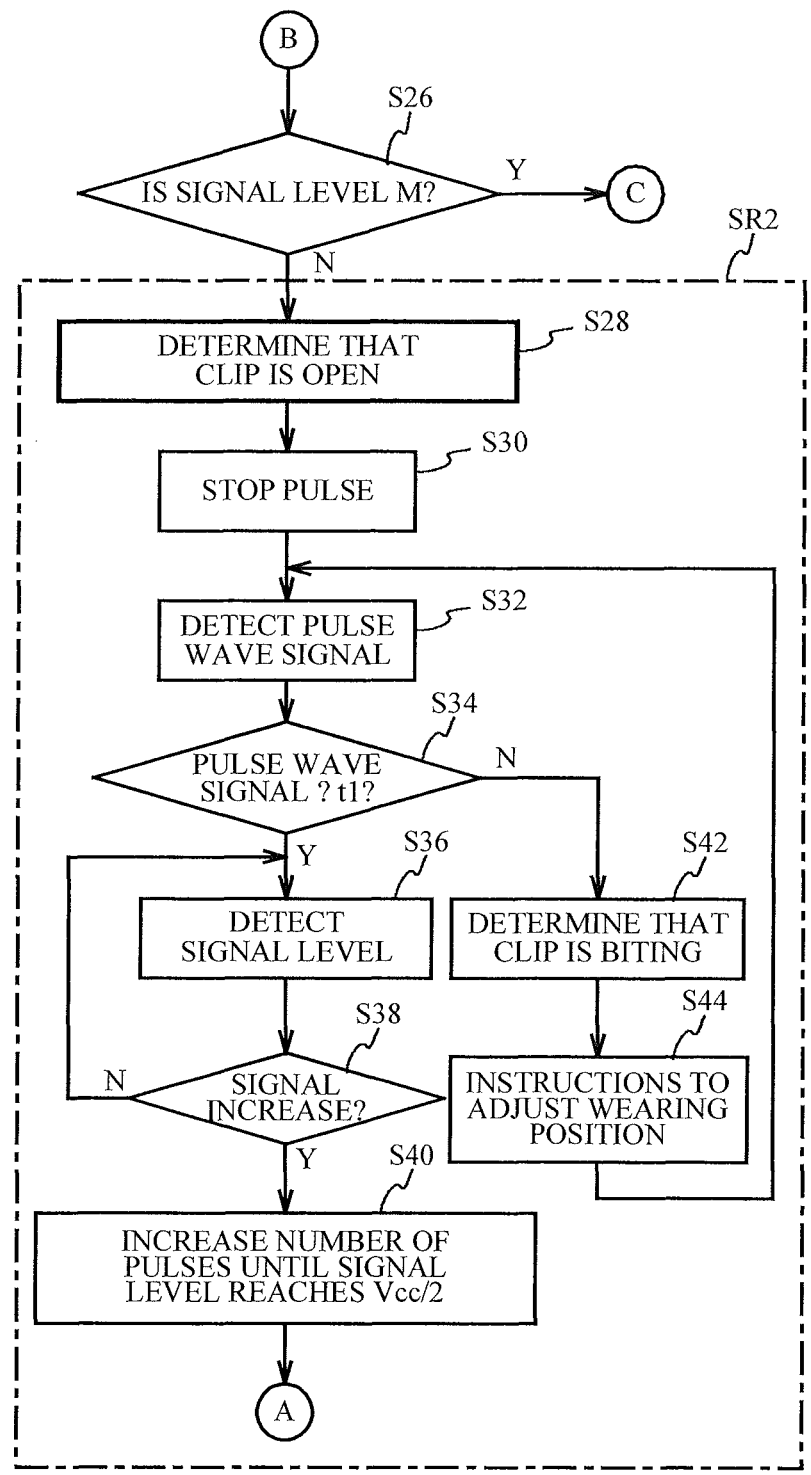
Figure 5C:
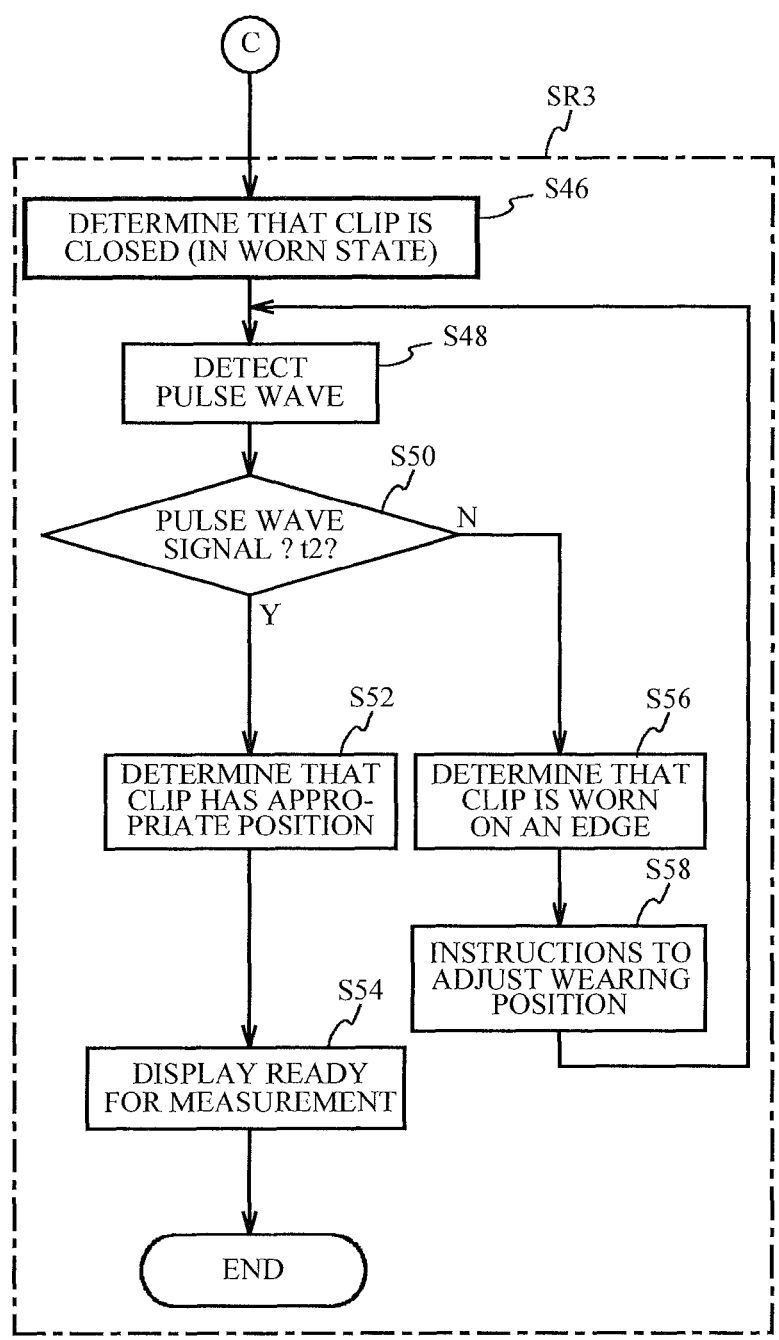

A description is now given, with reference to flowchages of FIGS. 5A through 5C, of a process of the photoelectric sphygmograph measurement device 100 until the measurement of pulse wave is started (restarted) from an initial state in which the measurement of pulse wave is not carried out. The process illustrated in FIGS. 5A through 5C is mainly performed by the control circuit 31.

In step S10, the control circuit 31 determines whether the level of the demodulated signal is high (H) (see FIG. 4). When the answer of step S10 is YES, the control circuit 31 moves to a not-worn (closed state) sub routine SR1, and determines that the ear clip part 10 is now in the closed state (not worn state) in step S12.

Next, the control circuit 31 causes wearing instructions to be displayed on the display device 5 of the ear clip part 10 via the display part 43 at step S14. Then, the control circuit 31 detects the signal level in step S16, and determines whether the signal level is equal to or greater than a reference value in step S18. The reference value may be equal to half the maximum value (Vcc) of the signal level, that is, Vcc/2.

When the answer of step S18 is YES, that is, when the signal level is equal to or higher than Vcc/2, the control circuit 31 moves to step S20 and stops pulse emission via the pulse emission circuit 211. Since the pulse emission is stopped, power consumption in the state that the ear clip part 10 is not worn may be reduced.

In contrast, when the answer of step S18 is NO, that is the signal level is lower than Vcc/2, the control circuit 31 moves to step S22 and executes the pulse emission via the pulse emission circuit 211. In step S24, the control circuit 31 determines whether the degree of increase of the signal level by the pulse emission has a change as compared to the past state. A change in the degree of increase of the signal level supposes a case where a certain change takes place from the not-worn state. For example, such a change appears when the ear clip part 10 is worn on the ear.

Figure 6A:
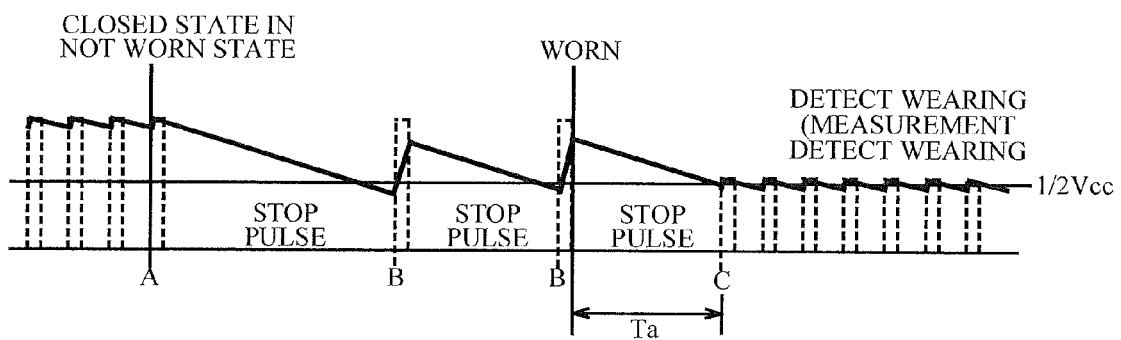
FIG. 6A illustrates an exemplary pulse emission observed when an ear clip part is changed from a state in which it is not worn and is closed to another state in which it is worn.

Steps S16, S18, S20 and S22 are repeated until the answer of step S24 becomes YES, that is, a change appears in the degree of increase of the signal level. This repetitive process is illustrated in FIG. 6A. It is seen from FIG. 6A that the pulse emission is stopped as of time A when the ear clip part 10 is in the closed state (not worn state), and is executed at time B in order to increase the signal level when the signal level becomes lower than Vcc/2. That is, according to the present embodiment, the pulse emission timing is controlled so that the signal level converges on Vcc/2 when the ear clip part 10 is not worn and is in the closed state.

Turning to FIG. 5 again, the process returns to step S10 when the answer of step S24 is YES, that is, in a case where a degree of increase of the signal level that is different from that in the past pulse emissions (the pulse emissions at times B appears, as illustrated at time C in FIG. 6A.

In contrast, when the answer of step S10 is NO, the process proceeds to step S26 in which the control circuit 31 determines whether the signal level is a medium value M, which may have a range as illustrated in FIG. 4. When the answer of step S26 is NO, that is, when the signal level is lower than the medium level M and is a low level L, which may have a range as illustrated in FIG. 4, the control circuit 31 moves to a non-worn (open state) sub routine SR2. In this sub routine SR2, the control circuit 31 determines whether the ear clip part 10 is in the open state (not-worn state) in step S28.

Next, in step S30, the control circuit 31 stops the pulse emission. Then, the control circuit 31 detects the amplitude level of the pulse signal in step S32, and determines whether the amplitude level of the pulse signal is equal to or higher than a threshold value t1 in step S34. When the answer of step S34 is NO, the control circuit 31 executes step S42 and determines that the ear clip part 10 is in the ear biting state. In step S44, the control circuit 31 displays instructions to adjust the position of the ear clip part 10 on the display device 5 via the display part 43. Then, the process returns to step S32. The steps S32, S34, S42 and S44 are sequentially repeated until the testee adjusts the ear biting state of the ear clip part 10 appropriately.

Figure 6B:
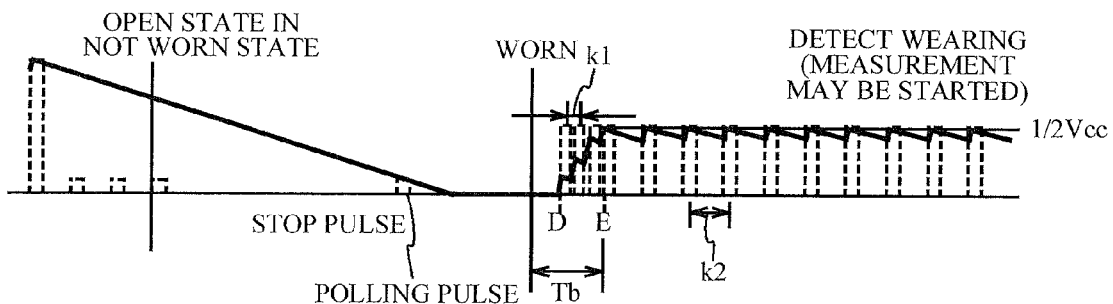
FIG. 6B illustrates an exemplary pulse emission observed when the ear clip part is change from a state in which it is not worn and is open to another state in which it is worn.

In contrast, when the amplitude level of the pulse signal exceeds the threshold value t1, the control circuit 31 moves to step S36 and detects the signal level. The detection of the signal pulse is performed by emitting polling pulses and detects the signal level obtained at each time. In step S38, the control circuit 31 determines whether the signal level thus detected has increased, as compared to the previous signal levels. When the answer of this determination is NO, the steps S36 and S38 are repeated until the answer becomes YES. The process proceeds to step S40 when the answer becomes YES. The answer of step S38 is YES, when an increase in the signal level is confirmed after the ear clip part 10 is in the open state (after step S28). In FIG. 6B, the answer of step S38 becomes YES at time D.

In step S40, the control circuit 31 executes a control to emit an increased number of pulses until the signal level reaches the reference value (Vcc/2) after the increase in the signal level is confirmed (from time D to time E in FIG. 6B). That is, the light pulses are emitted at emission intervals ($k_1$ in FIG. 6B) shorter than the emission intervals ($k_2$ in FIG. 6B) of light pulses used in the pulse measurement. The increased number of pulses reduces the time Tb necessary to obtain a signal level of Vcc/2. After the step S40 is finished, the process returns to step S10.

When the answer of step S26 is YES, that is, when the signal level is medium (M), the control circuit 31 moves to step S46 of a wearing sub routine SR3. In step S46, the control circuit 31 determines that the ear clip part 10 is worn, in other words, the ear clip part 10 is in the closed state.

The control circuit 31 detects the amplitude level of the pulse signal in step S48, and determines whether the amplitude level is equal to or higher than the predetermined threshold value $t_2$ in step S50. When the answer of step S50 is NO, the control circuit 31 moves to step S56 and determines that the ear clip part 10 is worm on an edge of the ear of the testee.

In step S58, the control circuit 31 causes instructions to adjust the position of the ear clip part 10 to be displayed on the display device 5 via the display part 43, and returns to step S48. Steps S48, S50, S56 and S58 are sequentially repeated until the testee adjusts the position of the ear clip part 10 appropriately and the answer of step S50 becomes YES.

In contrast, when the answer of step S50 is YES, the control circuit 31 moves to step S52, and determines that the ear clip part 10 is worn on an appropriate position. In subsequent step S54, the control circuit 31 sends a message indicating that the measurement device is ready for measurement including wearing of the ear clip part 10 to the display device 5 via the display part 43. Then, the control circuit 31 ends all the process of the flowchart of FIG. 5. When all the process of the flowchart is completed, the photoelectric sphygmograph measurement device is ready for starting or restarting the measurement. The pulse wave signal analyzing part 42 in the computer 4 illustrated in FIG. 1 carries out the measurement of pulse wave by referring to the amplitude level output from the AC amplifier circuit 224.

In the embodiment, a control part is configured to include the analog circuit 2, the digital circuit 3 and the computer 4.

Figure 7A:
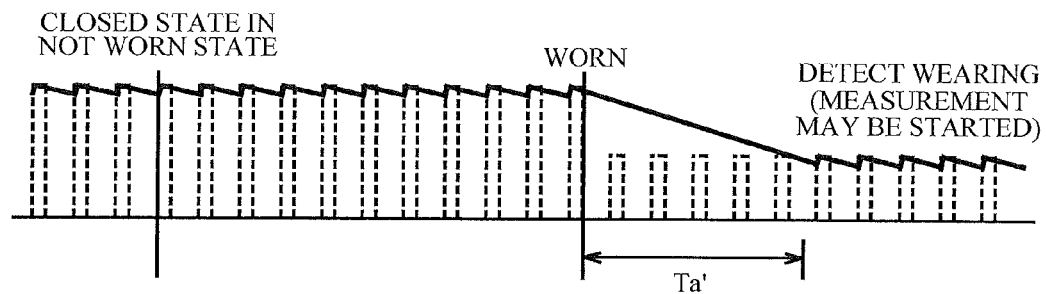
FIGS. 7A and 7B illustrate pulse emissions of a comparative example related to those of FIGS. 6A and 6B, respectively.

As described above, in the case where the charge accumulated in the light receiving element 12 becomes equal to or smaller than the predetermined amount while the light emitting element 11 is disabled, the light emitting element 11 is driven so that the charge accumulated in the light receiving element 12 converges on the predetermined amount (which sets the signal level equal to Vcc/2). It is thus possible to maintain the charge at Vcc/2 or close thereto while the light emitting element 11 is disabled in an interrupt of the measurement. It is thus possible to restart the measurement quickly when the restart is requested. This is now described in more detail by comparing FIG. 6A and FIG. 7A with each other. FIG. 7A illustrates an exemplary case where the pulse emission is not stopped even when the ear clip part is not worn and is in the closed state. In FIG. 6A, the repetition of pulse emission is reduced so that the signal level converges on Vcc/2. Thus, the measurement may be restarted by time Ta that is shorter than time Ta' illustrated in FIG. 7A after the ear clip part 10 is worn on the ear. That is, the control illustrated in FIG. 6A reduces the time Ta it takes to wear the ear chip part 10 on the ear and start the measurement. It is supposed that the time Ta' is a few seconds because the level of the pulse wave signal is as low as 1/100 or lower and the frequency thereof is as low as 0.5~4 Hz. The control in FIG. 6A reduces the number of times of pulse emission, as compared to that in FIG. 7A, and consumes a reduced amount of electricity.

Figure 7B:
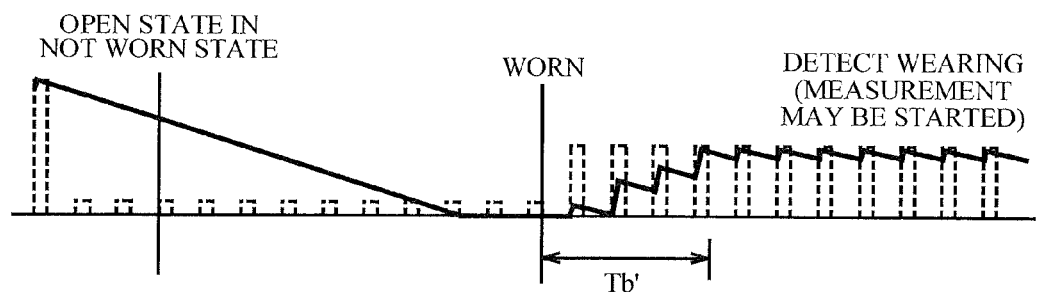

According to the embodiment, the light emitting element 11 is driven so that the charge accumulated in the light receiving element 12 converges on the predetermined amount (which sets the signal level equal to Vcc/2) in the case where the light receiving element 12 changes to the light receivable state from the state in which the light receiving element 12 is not capable of receiving the light pulses from the light emitting element 11. It is thus possible to quickly start the measurement of pulse wave after the light receiving element 12 changes to the light receivable state. This is now described in more detail by comparing FIGS. 6B and 7B with each other. FIG. 7B illustrates an exemplary case where the pulse emission is not stopped even when the ear clip part is not worn and is in the open state. The signal levels have similar behaviors in the open state with the ear clip part not being worn in FIGS. 6B and 7B. After it is determined that the ear clip part is worn, the control illustrated in FIG. 6B increases the number of pulses, so that a time Tb necessary for the signal level to converge on Vcc/2 can be reduced, as compared to a similar time Tb' in FIG. 7B. Further, the embodiment reduces the number of times of pulse emission in the open state with the ear clip part not being worn, and reduces electricity consumed in pulse emission. In the open state with the ear clip part not being worn, originally, the light emitted by the light emitting element 11 is not incident to the light receiving element 12. Thus, the measurement accuracy is not affected by reducing the number of times of pulse emission.

In the embodiment, instructions to wear the ear clip part 10 again (alarm) are displayed on the display device 5 in the case where the signal level is referred to and it is determined that the ear chip part 10 is not yet worn or is not worn appropriately (for example, the ear clip part 10 bites the ear strongly or is worn on an edge of the ear). Thus, the user is guided to wear the ear chip part 10 on the ear quickly and appropriately. It is thus possible to suppress unwanted vibrations and external light that lead to noise when the testee is taking exercise and to improve the accuracy of measurement of the pulse wave.

In the embodiment, the signal forming circuit 22 has the high-pass filter circuit 222. Thus, it is possible to effectively remove the influence of external light when the user is taking exercise and measure the pulse wave reliably even when the user is running while light is falling thereon through the trees or in the shade.

In the embodiment, the signal forming circuit 22 is configured to have the peak hold type demodulation circuit 223 that demodulates the output signal of the light receiving element 12 and the AC amplifier circuit 224 that amplifies the pulse wave signal from the peak hold type demodulation circuit 223. The wearing state of the ear clip part 10 (the relationship between the light emitting element 11 and the light receiving element 12) is detected by using the output of the peak hold type demodulation circuit 223 and the output of the AC amplifier circuit 224. The peak hold type demodulation circuit 223 uses the rectifying function of the diode and passes only positive signals having the predetermined level or higher. This avoids the use of analog switch. The wearing state of the ear clip part 10 is identified by using the demodulated signal output from the peak hold type demodulation circuit 223. It is thus possible to simplify the configuration involved in signal processing and speed up the signal processing. Also, the wearing state of the ear clip part 10 is identified by using the signal level of the demodulated signal that has not passed through any delay element such as the low-pass filter or the AC amplifier. It is thus possible to directly identify the wearing state from the data train having the above signal level.

The above description of the embodiment is directed to the ear clip type of photoelectric sphygmograph measurement device. However, the configuration and method of the ear clip type may be applied to another type of sphygmograph measurement device, which may be worn on a finger.

In the above embodiment, the reference value used to determine pulse emission is Vcc/2 (step S18 in FIG. 5), the value used to identify the timing of ending the control to emit an increased number of pulses is also Vcc/2 (step S40 in FIG. 5). However, these values are not limited to the above but appropriately selected values may be used.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various change, substitutions, and alterations could be made hereto without departing from the spirit and scope of the invention.

What is claimed is:

1. A photoelectric sphygmograph measurement device comprising:
    a light emitting circuit configured to emit light pulses;
    a light receiving circuit configured to have a light receiving element that receives the light pulses emitted by the light emitting circuit, to produce an output signal corresponding to the light pulses received by the receiving element, and to output the output signal; and
    a control circuit configured to drive the light emitting circuit to emit the light pulses and perform a pulse wave measurement based on the output signal of the light receiving circuit,
    wherein the control circuit is configured to:
    determine whether a signal level of the output signal of the light receiving circuit becomes less than a predetermined level while emission of the light pulses from the light emitting circuit is stopped by the control circuit; and
    drive the light emitting circuit to emit the light pulses until the signal level of the output signal of the light receiving circuit becomes equal to or greater than the predetermined level and less than a first signal level, which is obtained when the light pulses emitted by the light emitting circuit are received directly by the light receiving element, when the control circuit has determined that the signal level of the output signal of the light receiving circuit becomes less than the predetermined level,
        wherein the control circuit is configured to:
            determine whether the light receiving element changes to a first state from a second state, the light receiving element being capable of receiving the light pulses in the first state, the light receiving element being incapable of receiving the light pulses in the second state; and drive the light emitting circuit to emit the light pulses until the signal level of the output signal of the light receiving circuit reaches the predetermined level.

2. The photoelectric sphygmograph measurement device according to claim 1, wherein the control circuit is configured to:

cause the light emitting circuit to temporarily stop emitting the light pulses during a time when the light pulses emitted by the light emitting circuit are received directly by the light receiving element:

determine whether the signal level of the output signal of the light receiving circuit becomes less than the predetermined level after the light emitting circuit is caused to temporarily stop emitting the light pulses and enable the light emitting circuit to emit the light pulses until the signal level of the output signal becomes equal to or greater than the predetermined level and less than the first signal level when the control circuit has determined that the signal level of the output signal of the receiving circuit becomes less that the predetermined level.

3. The photoelectric sphygmograph measurement device according to claim 1, wherein when the light receiving element changes to the second state from the first state, the control circuit drives the light emitting circuit to emit the light pulses at intervals shorter than intervals used in the pulse wave measurement until the signal level of the output signal of the light receiving circuit reaches the predetermined level.

4. The photoelectric sphygmograph measurement device according to claim 1, wherein the control circuit includes a peak hold type demodulation circuit configured to demodulate the output signal of the light receiving circuit, and an extraction circuit configured to extract an amplitude of a pulse wave signal output from the peak hold type demodulation circuit, the control circuit identifies a state of the light emitting circuit and a state of the light receiving circuit based on the pulse wave signal from the peak hold type demodulation circuit and the amplitude of the pulse wave signal.

* * * * *